United States Patent
Frisch et al.

(10) Patent No.: US 10,254,253 B2
(45) Date of Patent: Apr. 9, 2019

(54) SYSTEM AND METHOD FOR DETECTING AND PROFILING RODENT ACTIVITY USING DETECTED ULTRASONIC VOCALIZATIONS

(71) Applicant: AP&G Co., Inc., Brooklyn, NY (US)

(72) Inventors: Jeffrey Frisch, Brooklyn, NY (US); Jonathan Frisch, Brooklyn, NY (US)

(73) Assignee: AP&G Co., Inc., Bayonne, NJ (US)

( * ) Notice: Subject to any disclaimer, the term of this patent is extended or adjusted under 35 U.S.C. 154(b) by 146 days.

(21) Appl. No.: 15/248,655

(22) Filed: Aug. 26, 2016

(65) Prior Publication Data

US 2017/0059532 A1 Mar. 2, 2017

Related U.S. Application Data

(60) Provisional application No. 62/210,049, filed on Aug. 26, 2015.

(51) Int. Cl.
| | |
|---|---|
| *G01N 29/30* | (2006.01) |
| *A01M 31/00* | (2006.01) |
| *G01N 29/14* | (2006.01) |
| *G01N 29/24* | (2006.01) |
| *G01N 29/42* | (2006.01) |
| *G01N 29/44* | (2006.01) |

(52) U.S. Cl.
CPC ........... *G01N 29/30* (2013.01); *A01M 31/002* (2013.01); *G01N 29/14* (2013.01); *G01N 29/2481* (2013.01); *G01N 29/42* (2013.01); *G01N 29/4436* (2013.01)

(58) Field of Classification Search
CPC . A01M 31/002; G01N 29/14; G01N 29/2481; G01N 29/30; G01N 29/42; G01N 29/4436
See application file for complete search history.

(56) References Cited

U.S. PATENT DOCUMENTS

| | | | | |
|---|---|---|---|---|
| 9,638,800 | B1* | 5/2017 | Skowronek | G08B 21/0469 |
| 2005/0049877 | A1* | 3/2005 | Agranat | A01K 11/008 |
| | | | | 704/270 |
| 2008/0270172 | A1* | 10/2008 | Luff | G06Q 30/02 |
| | | | | 705/1.1 |
| 2014/0192622 | A1* | 7/2014 | Rowe | G01S 5/28 |
| | | | | 367/117 |
| 2017/0071190 | A1* | 3/2017 | Lewis | A01M 31/002 |

\* cited by examiner

*Primary Examiner* — Francis C Gray
(74) *Attorney, Agent, or Firm* — Amster, Rothstein & Ebenstein LLP

(57) ABSTRACT

A system for detecting rodent activity in an area. A series of detectors that calibrated to detect rodent vocalizations are placed in a geographic area. One or more of the detectors detect rodent vocalizations and transmits data notifying a central computer of detected vocalizations. The computer is provided with a program that generates a report of incidences and locations of detected vocalizations.

2 Claims, 4 Drawing Sheets

SYSTEM AND METHOD FOR DETECTING AND PROFILING RODENT ACTIVITY USING DETECTED ULTRASONIC VOCALIZATIONS

RELATED APPLICATION

The current application claims the benefit of U.S. Prov. Appl. Ser. No. 62/210,049 filed Aug. 26, 2015—the contents of which are incorporated by reference herein.

FIELD OF THE INVENTION

The invention relates to the field of rodent detection, more specifically to a system comprising a series of specifically calibrated sound sensors to detect known rodent frequencies. The sensors are integrated with computer system to determine locations of rodent activity.

BACKGROUND OF THE INVENTION

Early detection of rodent activity and the ability to precisely locate areas of infestation are of paramount importance to homeowners, business owners and other property owners. There is currently no effective method or system for the early detection of rodents. Rather, for most property owners, the earliest sign of rodents is the presence of droppings or physical identification. Additionally, there is no reliable method of determining or mapping specific areas of rodent infestation. There is therefore a need in the art for a system that sensitive to the early detection of rodents and which allows for a robust mapping and grading of areas of infestation.

SUMMARY OF THE INVENTION

The invention set forth herein is a system that employs a series of ultrasound sensors to detect known frequencies emitted by various rodents. Each ultrasound sensor in the series reports each instance of a detected frequency of interest to a central computer. Such system allows for the early detection of rodents and it further allows for a method of determining areas or sectors of rodent activity.

DETAILED DESCRIPTION OF THE INVENTION

Figure 1:
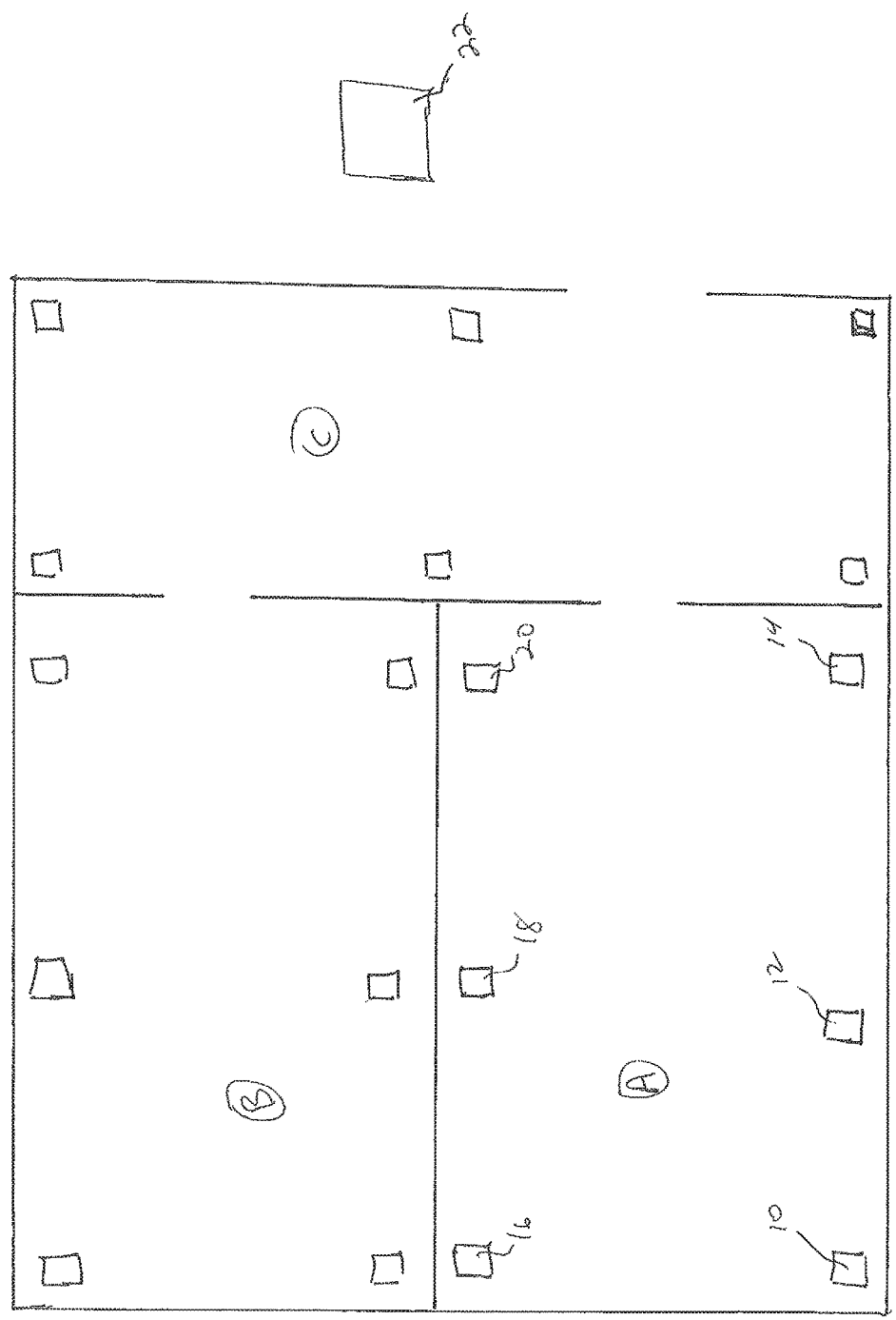
FIG. 1 is a schematic floor plan showing a system architecture according to a first embodiment of the invention.

The following is a detailed description of the preferred embodiments of the invention, reference being made to the drawings in which the same reference numerals identify the same elements of structure in each of the several figures. It should be noted that these drawings are merely exemplary in nature and in no way serve to limit the scope of the invention.

Both mice and rats engage in vocalization, most of which occurs in the ultrasonic range. Detecting such ultrasonic vocalizations (USV) may be useful in determining whether or not rodents are present in a building or facility. In addition, such information allows users to pinpoint where the highest incidence of rodent infestation may be found and it may also be used to gauge the effectiveness of treatment or abatement measures.

Rats typically emit two types of USVs—namely, a "22-kHz vocalization" and a "50-kHz vocalization." The 22-kHz vocalizations, are within a frequency range of 18-32 kHz and they have a sound pressure level of 65-85 dB. Such calls have an approximate duration of 300-4000 ms. The higher frequency, 50-kHz vocalizations, are within a frequency range of 32-96 kHz, with short durations of 30-50 ms. Mice, similarly, emit USVs in frequencies ranging from 30 to 110 kHz.

The invention herein comprises a series of ultrasound detectors that are calibrated to detect all the frequency ranges known to be emitted by mice and rats (e.g. 18-110 kHz). Each of the sensors is provided with a wired or wireless transmitter to communicate with a central computer. The detectors are programmed to transmit a message to the central computer each time it detects a frequency associated with a rodent.

FIG. 1 shows a floor plan of a facility that is outfitted with the inventive sensors according to an embodiment of the invention. As shown, the facility has three rooms (A, B and C). Six sensor units (10, 12, 14, 16, 18, and 20) are shown positioned in room A. As shown, unit 10 is in one corner, unit 14 is in an opposing corner and unit 12 is positioned roughly midway between units 10 and 14. A substantially mirroring unit configuration is shown on the opposing wall.

Each unit is provided with ultrasound sensing technology and is calibrated to detect frequencies known to be emitted by rodents. Each unit also is provided with a communication mechanism for communicating with a central computer 22. It will be understood by those of ordinary skill in the art that any of various wireless communication devices may be used to transmit incidences of detected rodent frequencies to a central computer. For example, wireless communication may be in the form of a Bluetooth transmitter, a WiFi transmitter, a cellular transmitter or any such similar transmission systems. In one embodiment, each unit automatically transmits a message to a central computer 22 each time a rodent frequency is detected. In another embodiment of the invention, each unit records the number of incidences of detected rodent frequencies and stores the information on a local storage medium. In some embodiments, the stored number of incidences are automatically sent from the units to the central computer 22 at predetermined intervals (e.g. once every 12 hours, once every 24 hours etc.).

In the embodiment shown in FIG. 1 each unit transmits data directly to a central computer 22. The central computer herein may comprise one or more processors and non-transitory computer-readable memory (e.g., local and/or remote memory) having stored thereon computer-readable instructions to perform the processes described herein with respect to each device and/or computer system. In embodiments, various processing may be performed by particularly programmed software agents or software modules. Each device (e.g. sensor and/or bait stations) and/or central computer may store data in its respective memory, which may be organized in one or more databases. Each device and/or computer system may also have one or more input devices (e.g., touchscreen, pointer device, mouse, keyboard, microphone, camera, video camera, to name a few) and/or one or more output devices (e.g., display screens, projectors, speakers). In embodiments, computer systems may comprise one or more servers or server farms, which may not have physical input or output devices directly connected thereto or embedded therein.

In the embodiment shown in FIG. 1, a user is able to determine which rooms and/or sectors of the facility may have rodent infestations or populations. That is, each unit has a unique identifier (e.g. an IP address) so that when it transmits its data to the central computer, the computer may identify which unit detected rodent frequencies.

In embodiments of the invention each detector device may include one or more communication portals. Accordingly, the detector devices may be operatively connected directly, e.g., via wired or wireless communications, and/or indirectly, e.g., via a data network such as the Internet, a telephone network, a mobile broadband network (e.g., a cellular data network), a mesh network, a local area network (LAN) (including a wireless local area network, e.g., a Wi-Fi network), a wide area network (WAN), a metropolitan area network (MAN), and/or a global area network (GAN), to name a few. Data networks may be provided via wired and/or wireless connections. Data networks may be public or private. Accordingly, data networks may be open or closed, such as requiring authorized access, specific communication connections, or specialized hardware and/or software. In embodiments, any combination of communications channels may be utilized.

In the embodiment shown in FIG. 1, if the sensors in room A transmit data related to detected rodent frequencies, and the units in rooms B and C do not transmit such data, then room A may be identified as room having a rodent infestation.

In embodiments of the invention, each of the sensors is provided with geolocation device. The location of each device is transmitted to a central computer to create a "virtual map" of an area under surveillance. Captured rodent vocalizations may, thus, be traceable to a specific coordinates (obtained by the geolocation) device. The computer using a specialized software program generates a virtual map of rodent activity.

Figure 2:
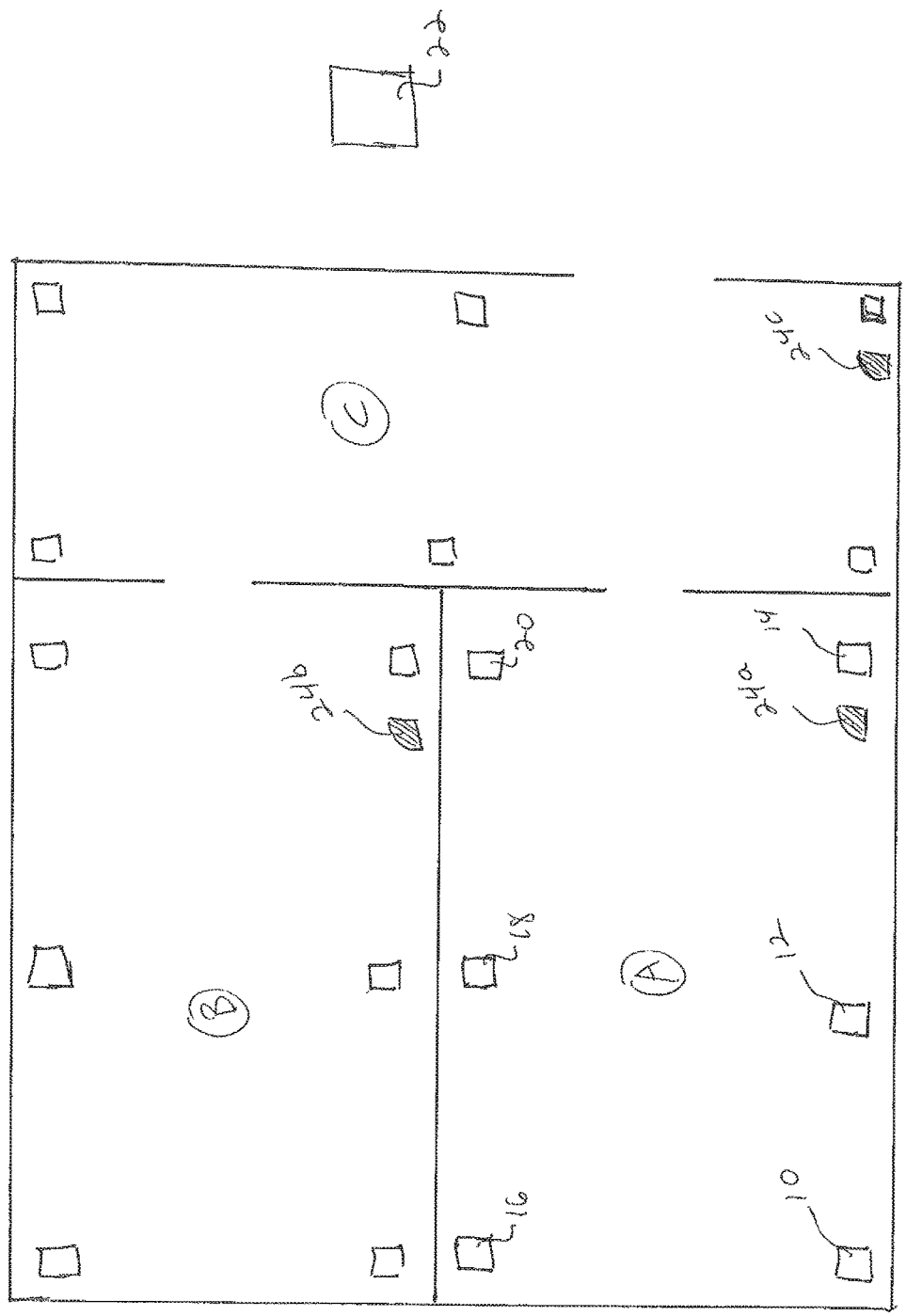
FIG. 2 is a schematic floor plan showing a system architecture according to a second embodiment of the invention.

FIG. 2 shows a similar system configuration as that shown in FIG. 1, the difference being that individual units do not directly transmit data to a central computer 22, but rather different series of units transmit signal to different respective wireless routers. The various wireless routers, in turn, transmit data to the central computer 22.

For example, as shown in FIG. 2, the units in room A transmit data to router 24a, the units in room B transmit data to router 24b and the units in room C transmit data to router 24c. The various units transmit data corresponding to detected rodent signals to the associated routers and the routers transmit the data to the central computer 22.

In the embodiment shown in FIG. 2, a user is able to determine which rooms and/or sectors of the facility may have rodent infestations or populations. That is, each router has a unique identifier or IP address so that when it transmits its data to the central computer, the computer may identify which router sent data concerning detected rodent frequencies. In the example shown, if the router in room A transmit data related to detected rodent frequencies, and the routers in rooms B and C do not transmit such data, then room A may be identified as room having a rodent infestation. Similarly, levels of activity may be detected and monitored by evaluating relative incidences of rodent frequencies in different rooms or sectors.

Figure 3:
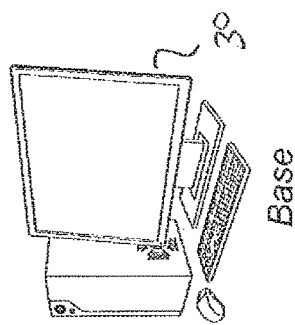
FIG. 3 shows system components for a rodent trapping and surveillance system according to an embodiment of the invention.
Figure 3:
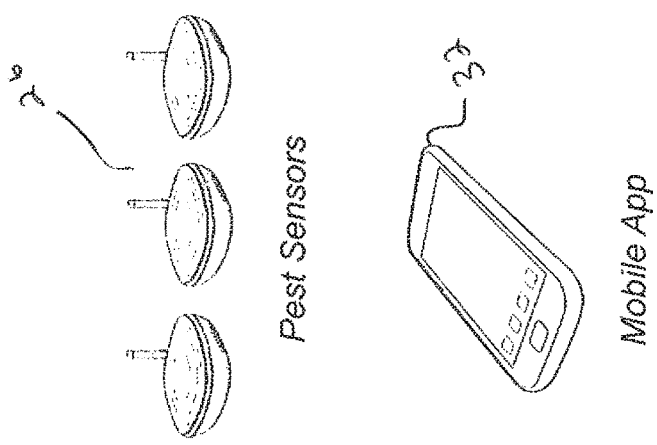
Figure 3:
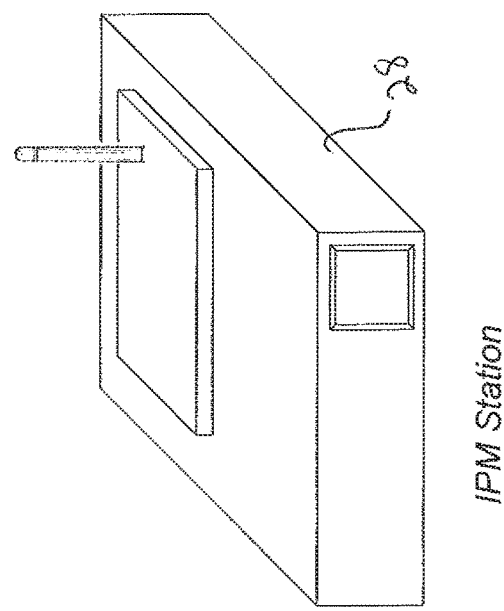

FIG. 3 shows system components for a rodent surveillance and trapping system according to an embodiment of the invention. As shown, the system includes one or more sensors 26, such as ultrasound sensors, motion sensors or the like. The system may additionally or alternatively include one or more bait stations 28 or traps that have sensing systems that sense when a rodent has been caught. For example, in an embodiment of the invention, bait station 28 is provided with an internal motion sensor, which registers each time it senses the motion of a rodent entering therein and sends an electronic message or notice to a central computer via wireless communication alerting a user that a rodent is in the station. Both, the sensors 26 and the bait station 28 send signal to a computer 30 via wireless communication. The integrated system of this embodiment allows a user to remotely remain apprised of when a rodent is caught (or has entered a bait station) and when chatter of other rodents has been detected. For example, information may be sent to a local computer or to a server that is accessible via a website or mobile application running on a smartphone 32 or such similar mobile device.

It will be understood by those of ordinary skill in the art that each sensor 26 and bait station 28 or trap may be provided with a unique identifier such as an IP address, thereby allowing a user to know which sensors (at which location) sensed a rodent and which bait stations/traps were visited by rodents.

Figure 4:
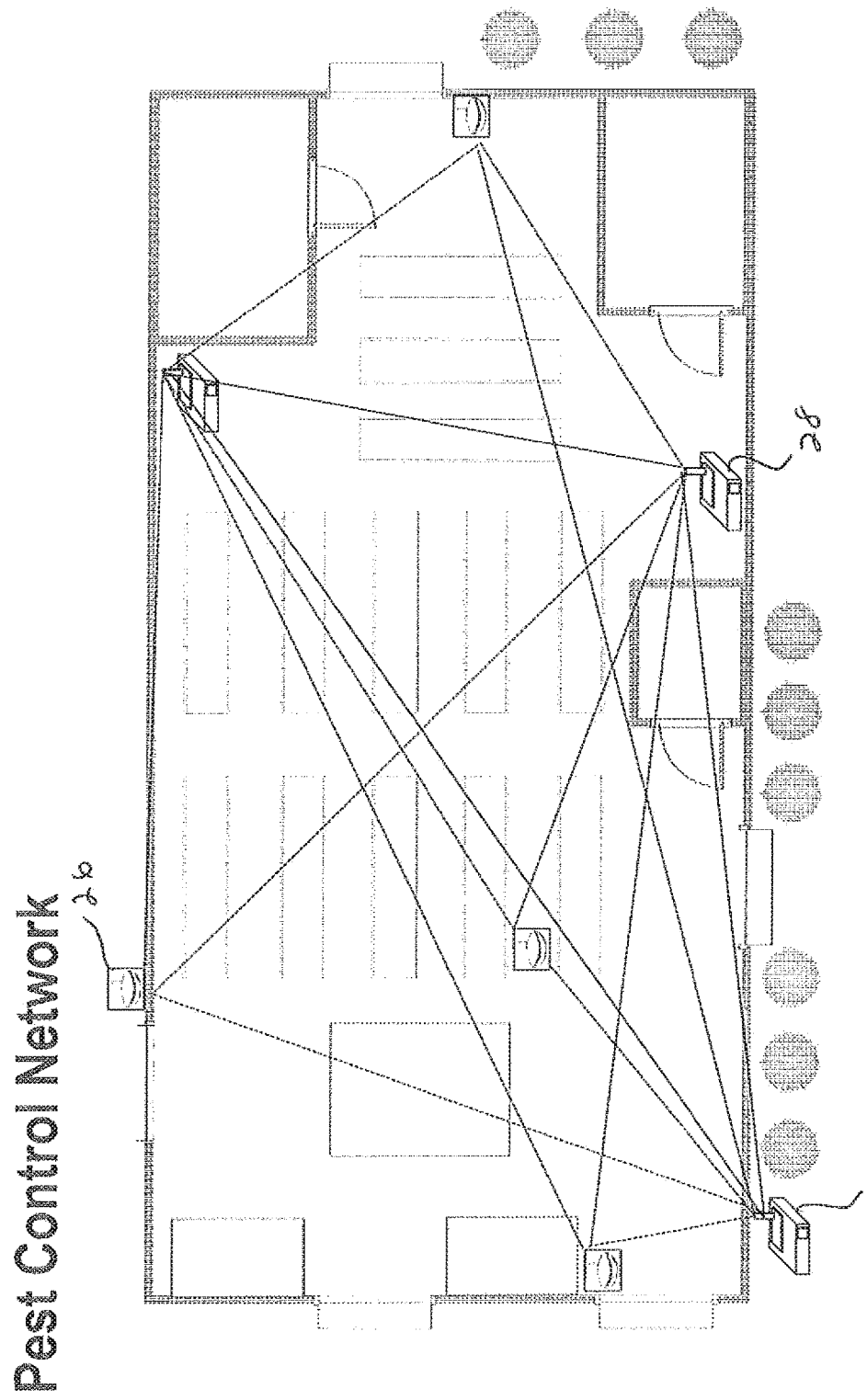
FIG. 4 shows a schematic floor plan for a rodent trapping and surveillance system according to an embodiment of the invention.

FIG. 4 shows a floor plan of a property where the inventive trapping and surveillance system is deployed according to an embodiment of the invention. As shown, a series of sensors 26 and trap or bait stations 28 are placed throughout the facility. A bait station 28a is shown outside of the facility. Each of the sensors 26 and bait stations 28 communicate with a central computer. A user may access the central computer (either directly, through an associated website and/or through a mobile software application) to view reports of rodent activity (such as ultrasonic vocalizations or incidences of rodents entering stations).

Having described this invention with regard to specific embodiments, it is to be understood that the description is not meant as a limitation since further modifications and variations may be apparent or may suggest themselves to those skilled in the art. It is intended that the present application cover all such modifications and variations.

What is claimed is:

1. A system for detecting rodent activity, comprising:
   a series of ultrasound detectors that are calibrated to detect frequency ranges associated with vocalizations that are emitted by rodents;
   a central computer comprising one or more processors and computer-readable memory, the computer-readable memory comprising computer-readable instructions;
   the central computer adapted to receive information from each of the ultrasound detectors relating to detected rodent vocalizations;
   the one or more processors configured to read the computer-readable instructions from the computer-readable memory to generate a map of a geographic area, the map showing areas of detected vocalizations.

2. A method of determining rodent activity, comprising the steps of:
   providing a series of detectors in different positions within a geographic area;

at least one of the detectors detecting a rodent vocalization;
transmitting by the at least one of the detectors to a computer data relating to a detected vocalization;
registering in the computer an incidence of a detected vocalization; and
displaying a report relating to the incidence of a detected vocalization.

\* \* \* \* \*